United States Patent [19]

Uitti

[11] 4,039,602
[45] Aug. 2, 1977

[54] ETHYLBENZENE DEHYDROGENATION PROCESS

[75] Inventor: Kenneth D. Uitti, Bensenville, Ill.

[73] Assignee: Universal Oil Products Company, Des Plaines, Ill.

[21] Appl. No.: 574,987

[22] Filed: May 6, 1975

[51] Int. Cl.² .................... C07C 15/00; C07C 15/10
[52] U.S. Cl. ............................................. 260/669 R
[58] Field of Search ................................... 260/669 R

[56] References Cited
U.S. PATENT DOCUMENTS

| | | | |
|---|---|---|---|
| 2,851,502 | 9/1958 | Bowman et al. | 260/669 R |
| 3,294,856 | 12/1966 | Huckius | 260/669 R |
| 3,492,222 | 1/1970 | Van Tassell | 208/321 |
| 3,515,764 | 6/1970 | Hallman et al. | 260/669 R |
| 3,515,765 | 6/1970 | Berger | 260/669 R |
| 3,515,766 | 6/1970 | Root et al. | 260/669 R |
| 3,515,767 | 6/1970 | Carson et al. | 260/669 R |
| 3,847,968 | 4/1974 | Hughes | 260/669 R |

FOREIGN PATENT DOCUMENTS 1,301,874   1/1973   United Kingdom ............ 260/669 R

OTHER PUBLICATIONS

Handbook of Chem & Phy–55th Ed.–p. C494.
Condensed Chemical Dictionary–8th Ed.–p. 673, (Hawley-Ed.).

Primary Examiner—O. R. Vertiz
Assistant Examiner—Eugene T. Wheelock
Attorney, Agent, or Firm—James R. Hoatson, Jr.; Robert W. Erickson; William H. Page, II

[57] ABSTRACT

A process for the dehydrogenation of alkylaromatic hydrocarbons, such as ethylbenzene, in which a water stream formed by condensing and separating the effluent of the reaction zone is treated for the removal of alkenylaromatic hydrocarbons by passage through a liquid-liquid extraction zone, and the alkenylaromatic hydrocarbons are then recovered by admixing the extract stream with the effluent as part of the cooling performed before the effluent is passed into a liquid phase separation zone.

3 Claims, 1 Drawing Figure

U.S. Patent
Aug. 2, 1977
4,039,602
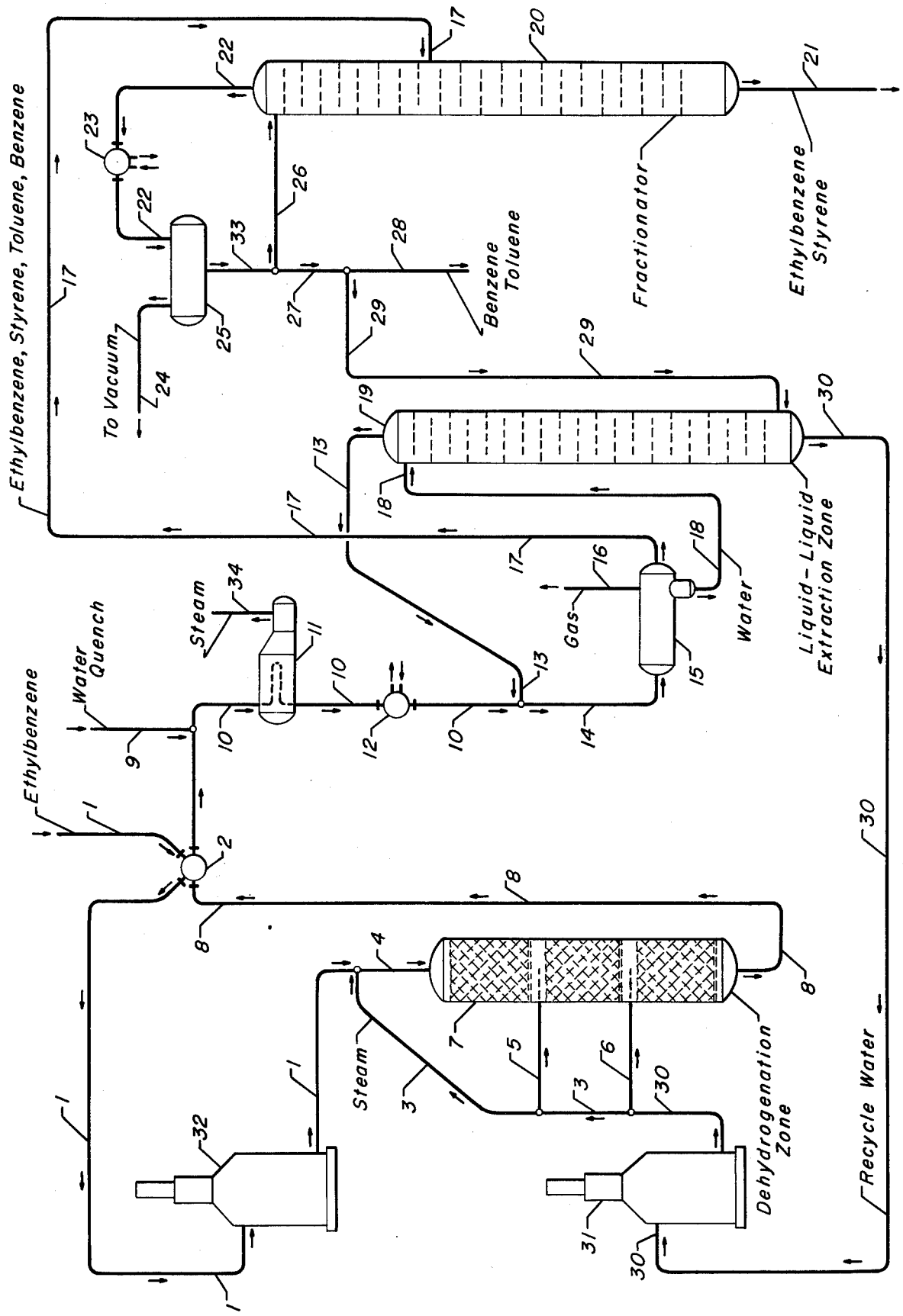

ETHYLBENZENE DEHYDROGENATION PROCESS

FIELD OF THE INVENTION

The invention relates to a process for the catalytic dehydrogenation of alkylaromatic hydrocarbons. The invention specifically relates to a catalytic process for the dehydrogenation of ethylbenzene to styrene wherein liquid-liquid extraction is used to remove styrene from the water stream formed by condensing and separating the effluent of the reaction zone.

DESCRIPTION OF THE PRIOR ART

The art of alkylaromatic hydrocarbon dehydrogenation is well developed as shown by the many commercial plants in operation and the wealth of literature in the field. Exemplary processes are shown in U.S. Pat. Nos. 3,515,765 and 3,515,766 (Cl. 260-269). Both of these references teach a process for the catalytic dehydrogenation of an alkylaromatic hydrocarbon, such as ethylbenzene, in which steam is passed through a reaction zone in admixture with the alkylaromatic hydrocarbon. The effluent of the reaction zone is cooled sufficiently to cause condensation of the water and heavier hydrocarbons. The effluent is then passed into a separator, and a water phase is removed and passed into a water stripper to effect the removal of the dissolved hydrocarbons.

In the former reference, the water purified in the stripper is heat-exchanged with the reaction zone effluent to form steam used for stripping in a fractionation column. The steam is then removed from the column as an overhead vapor containing undehydrogenated hydrocarbons and returned to the reaction zone. In the latter reference, the stripped water is passed through a filter to remove hydrocarbons not removed in the stripper. It is recognized that the 0.01 to 0.08 mole percent of non-aromatic hydrocarbons in solution and in suspension will eventually foul heat-exchangers and boilers used to generate steam. The use of the filter therefore facilitates the passage of the stripped water into a fired feed heater.

The effluent of the reaction zone is cooled in the art by heat exchanging the effluent with the feed stream and then quenched by admixture with liquid water. It is known to further cool the effluent by use of a condenser and by admixture with a liquid hydrocarbon stream derived from the stream of condensed liquid hydrocarbon products in the downstream vapor-liquid separator to which the effluent is charged. Heat has also been removed from the effluent stream by generating steam.

The prior art includes cooling the overhead vapor removed from the water stripper and combining this material with the reaction zone effluent stream at a point prior to the separator.

U.S. Pat. No. 3,492,222 (Cl. 208-321) presents a solvent recovery method for use in a liquid-liquid extraction process. Non-aromatic hydrocarbons are removed from an aqueous wash stream by contacting the wash stream with an aromatic hydrocarbon. This is performed to avoid contamination of an aromatic extract by the non-aromatic hydrocarbons when this water is utilized to form the stripping steam used in separating the aromatic extract from a rich solvent.

SUMMARY OF THE INVENTION

A process is provided for the catalytic dehydrogenation of ethylbenzene and other alkylaromatic hydrocarbons wherein the amount of energy consumed in removing styrene from the water condensed from the reaction zone effluent is reduced and the styrene is then recovered without the use of additional separation steps. The invention comprises passing the cooled and condensed effluent of a catalytic dehydrogenation zone into a phase separation zone, removing a water stream from the phase separation zone and passing it into a liquid-liquid extraction zone wherein it is contacted with a hydrocarbon solvent stream comprising benzene with removes styrene and ethylbenzene from the water stream, removing a hydrocarbon extract stream, which comprises benzene, water, ethylbenzene and styrene, from the extraction zone, and admixing this extract stream with the dehydrogenation zone effluent stream as part of procedure whereby the effluent stream is cooled. Preferably, the solvent stream is formed by fractionating the hydrocarbon phase formed in the phase separation zone.

DESCRIPTION OF THE DRAWING

The FIGURE illustrates one embodiment of the invention as it is used in a process for the dehydrogenation of ethylbenzene.

The ethylbenzene feed stream enters the process through line 1 and is heat exchanged in a feed-effluent heat exchanger 2 with the effluent of the dehydrogenation zone 7. The now heated ethylbenzene stream continues through line 1 into a heater 32 wherein it is raised to a temperature near that desired for the feed stream to the dehydrogenation zone. The feed stream continues through line 1 and is admixed with a stream of superheated steam from line 3 to form a net feed stream to the dehydrogenation zone which is passed through line 4. The net feed stream enters the dehydrogenation zone 7 and passes through a first bed of catalyst wherein a portion of the ethylbenzene is dehydrogenated, resulting in a lowering of the temperature of the reactants. A second stream of superheated steam is therefore passed into the dehydrogenation zone through line 5 and admixed with the reactants to raise them to the necessary temperature. The reactants are then passed through a second bed of catalyst and once again admixed with a stream of superheated steam entering through line 6 before passage through the final bed of catalyst. This results in the formation of a dehydrogenation zone effluent stream which is removed in line 8 and passed through the feed-effluent heat exchanger 2. The effluent stream is then admixed with a water stream from line 9 in order to quench the effluent stream and to limit polymerization of the styrene formed in the dehydrogenation zone. The quenched effluent stream then passes through line 10 into a steam generation zone 11, and low pressure steam is removed through line 34. This results in a further cooling of the effluent stream, which continues through line 10 and passes through a cooler 12. The now cooled effluent stream is then admixed with a hydrocarbon stream passing through line 13. At this point, substantially all of the heavier hydrocarbons and water in the effluent stream have been condensed, and the resulting mixed phase effluent stream passes through line 14 into a phase separation zone 15. An off-gas stream comprising hydrogen and light reaction by-products is removed through line 16.

The effluent stream divides into a hydrocarbon phase and an aqueous phase in the phase separation zone. The hydrocarbon phase is removed through line 17 and passed into a fractionator 20. The heavier ethylbenzene and styrene are removed from the fractionator through line 21, and an overhead vapor stream comprising benzene, toluene and lighter hydrocarbons is removed through line 22. This overhead vapor stream passes through a condenser 23 and then enters an overhead receiver 25 as a mixed phase stream. The uncondensed gases pass to a vacuum source through line 24. The condensed portion of the overhead vapor stream is withdrawn via line 33 and divided into a first portion which is passed into the fractionator 20 as a reflux stream carried in line 26 and a second portion removed in line 27. A portion of the overhead material carried in line 27 is again divided into a first portion removed in line 28 as the net overhead product, which is comprised of benzene and toluene. The remaining portion of the material passing through line 27 is diverted into line 29 for use as the solvent stream passed into a liquid-liquid extraction zone 19. The solvent stream rises through the extraction zone countercurrently to a descending water stream, which is formed by transferring the aqueous phase formed in the phase separation zone to the top of the extraction zone through line 18. This results in the transfer of styrene and ethylbenzene dissolved in the water stream into the solvent stream and thereby forms an extract stream comprising benzene, toluene, ethylbenzene and styrene which is removed in line 13. This extract stream is then used as the hydrocarbon stream which is admixed with the dehydrogenation zone effluent stream prior to its passage into the phase separation zone. The now treated water stream, which contains water, benzene and toluene is removed from the bottom of the extraction zone through line 30 and passed into a heater 31 to form the steam admixed with the ethylbenzene fed to the reaction zone.

DETAILED DESCRIPTION

Large amounts of styrene are produced commercially by the dehydrogenation of ethylbenzene. The dehydrogenation process is endothermic, and therefore the predominant processes for the production of styrene admix sizable amounts of superheated steam with the vaporized ethylbenzene before it is fed into the reaction zone. The superheated steam acts as a heat source which allows a greater amount of dehydrogenation to be performed in the catalyst bed before the temperature becomes too low for the reaction to proceed. The steam also acts as a diluent for the reaction products, which discourages polymerization. It is not desirable that these large amounts of water enter the fractionation zone downstream. The most feasible way to remove the water is to condense it. In order to condense out this water at the low pressure of the reaction zone effluent, it is necessary to also condense the heavier hydrocarbons. Therefore, most all of the water and the hydrocarbons having six or more carbon atoms are condensed. The substantially condensed effluent stream is then passed into a liquid phase separation zone or settler, wherein it separates into a hydrocarbonaceous phase and an aqueous phase. It is desirable to reuse the water which is separated by recycling the water to a steam generation zone because this reduces the necessity of treating additional make-up water, and it also eliminates the problem of disposal of the condensed hydrocarbon-containing water. The term "steam generation zone" is intended to refer to any boiler or waste heat steam generator, etc., wherein liquid water is converted to steam.

The water which is removed from the separation zone will have dissolved in it a varying amount of the hydrocarbons present in the separator. It will therefore contain a mixture of various aromatic hydrocarbons, such as ethylbenzene, styrene, benzene and toluene and various polymeric compounds normally referred to as tar. It is recognized in the art that the styrene, ethylbenzene and tar must be removed before this water stream can be reused for the generation of steam. If this is not done, these materials will cause a severe coking problem in the tubes of the superheater causing a rapid shutdown of the process. Furthermore, the styrene forms a polystyrene coating on the surface of feed-effluent heat exchanger tubes. This tends to plug the exchanger and to reduce its heat transfer efficiency. The prior art therefore treats the recycle water stream by first stripping substantially all of the lighter dissolved hydrocarbon materials from the recycle water stream. The overhead vapor produced by this operation may by condensed and recycled to the phase separation zone. The stripped water is then often passed through a filtration system to remove the remaining hydrocarbons, especially the high-boiling tar which is not removed in the stripping operation. This filtation often comprises the passage of the water stream through a bed of activated charcoal. The stripping of the recycle water stream consumes a fair amount of energy and therefore increases the utility costs of the overall process. This is an important factor when the present high cost of energy is considered.

It is an objective of this invention to provide a process for the dehydrogenation of ethylbenzene with reduced utility costs and wherein it is not necessary to strip the recycle water stream. It is a further objective of the invention to provide a process wherein hydrocarbons dissolved in the recycle water steam are removed and recovered in a facile and economic manner. The effluent of a dehydrogenation unit contains a large amount of low pressure steam which can be used for this relatively low temperature stripping operation, but which cannot be used in the higher temperature hydrocarbon separations. For this reason, the invention is most useful in an integrated petrochemical complex wherein there exists a use for low pressure steam. For example, it may be used on a benzene drying column on an alkylation unit producing the ethylbenzene fed to the dehydrogenation unit. Alternatively, the invention increases the amount of low pressure steam available for compression in steam conservation systems which provide high pressure steam.

The present invention resides in part in the realization that the removal of all hydrocarbons from the recycle water stream is not necessary, and that the problems of polymer formation in heat exchangers and coke buildup in boiler tubes can be avoided in a less costly manner by simply displacing undesirable hydrocarbons in an extraction zone instead of removing all hydrocarbons by stripping followed by filtration. It is only necessary to remove the $C_8$-plus alkylaromatic and alkenylaromatic hydrocarbons and tar. Benzene and toluene will normally pass through the boiler tubes unaffected, but can link up to form undesired biphenyls. Saturated cyclic compounds, paraffins and olefins will have a minimal detrimental effect as they tend to crack almost completely to methane and hydrogen in the presence of water. The present invention therefore comprises passing the recycle water stream into a liquid-liquid extraction zone wherein substantially all of the undesired alkylaromatic and alkenylaromatic hydrocarbons are removed from the water stream by contact with a solvent stream comprising hydrocarbons having little or no tendency to obstruct the boiler tubes by coke formation. As used herein, the term "substantially all" refers to a quantity or percentage equal to at least 90% and preferably 95% of the subject material. Likewise, the term "substantially free" is intended to indicate a molal percentage of less than 5% for the material referred to in the subject process stream. The concentration of dissolved benzene and toluene in the treated water will be fairly low and can be regulated by adjusting the temperature of the extraction zone.

The present invention also resides in part in (1) the recycling of the hydrocarbon extract stream from the extraction zone to the phase separation zone as a facile method of recovering the dissolved hydrocarbons, and, (2) in using the extract stream as a substitute for the hydrocarbon slip stream normally admixed with the effluent stream prior to passage into the phase separation zone. The extract material then becomes part of the hydrocarbonaceous phase formed in the phase separation zone and is passed into the fractionation zone. The present invention therefore comprises either admixing the extract stream produced in the extraction zone with the effluent stream or passing the extract stream directly into the phase separation zone. It is preferred that the extract stream be admixed with the effluent stream. It is specifically preferred that the extract stream is admixed with the effluent stream before the effluent stream enters the last cooler used in the condensation operation. This eliminates the need to control the diversion of the hydrocarbon slip stream from the hydrocarbon stream sent to the fractionation zone and somewhat simplifies the fabrication and internal structure of the phase separation zone.

Many different mechanical arrangements will perform the function of the liquid-liquid extraction zone, which is to provide the necessary contacting and admixture of the solvent stream and the recycle water stream to cause the transfer of substantially all of the undesirable hydrocarbons into the solvent. It may be a vertical extraction tower as shown in the drawing or a series of batch contacting operations comprised of mixing and settling zones. The extraction tower may use a rotating disk contactor or a pulsed mode of operation to promote extraction. The equipment and design methods needed for the construction and operation of the zone are within the knowledge of those skilled in the art. Detailed information can be obtained from such references as section 14 of the Fourth Edition of *The Chemical Engineers' Handbook*, McGraw-Hill, 1963, or the series of articles on pages 50 to 104 of *Chemical Engineering Progress*, (Vol. 62, No. 9), Sept. 1966. More specifically, the size of the extraction zone and the required rate of the solvent stream are set by the composition and flow rate of the recycle water stream, the desired composition of the product water stream, the efficiency of the contractor and the solubilities of the various components in the two contacted streams. It is preferred that the extraction zone is operated with countercurrent flow of the solvent and water streams.

As an example, to reduce the styrene concentration of a 380,000 lb/hr water stream from 580 ppm to 5.8 ppm in an extraction zone equivalent to one theoretical stage and operated at 150° F requires a benzene solvent stream of about 21,820 lb/hr. The treated water stream would contain about 379,940 lb/hr of water, 960 lb/hr of benzene and 2 lb/hr of styrene. The exact conditions used in the extraction zone will be set after a consideration of the temperature effect on solubilities, the unadjusted temperature of the chosen input streams and the desired temperatures of the effluent streams. Liquid-liquid extraction zones are normally run in a temperature range of from about 60° F to about 200° F and with a positive pressure ranging from about atmospheric to 200 psig. The extraction zone will often "float" on an upstream or downstream unit to ease pressure regulation problems. The pressure does not affect the extraction operation and is therefore chosen after a consideration of the pressure drop in the extractor, the cost of an extractor designed for a higher pressure and the volatility of the liquids.

From this example, it may be seen that the benzene solvent stream required is smaller than the water stream. Therefore, even if the extract stream is fractionated to recover the styrene, the utilities cost is reduced due to the smaller amount and the lower latent heat of the benzene stream. The capital costs of using the invention should be no more than using a stripper since the structure of the stripper is very similar to an extraction column, but also includes a reboiler and possibly an overhead condenser. Depending on the ease of the extraction, it may possibly be performed in a number of low cost contacting and settling chambers. These reduced costs are two of the advantages of the invention.

The solvent stream used in the extraction zone may be any suitable liquid possessing a good solubility for styrene or other undesired hydrocarbons and which does not cause excessive coking in the heating tubes. The solvent stream may therefore comprise low molecular weight paraffinic hydrocarbons such as heptane, hexane, pentane or butane or a mixture of them. The solvent stream may also comprise benzene and toluene, and may therefore be a mixture of benzene and paraffinic hydrocarbons having from four to six carbon atoms per molecule. A suitable solvent stream may be readily obtained from the fractionation zone in which the styrene is recovered by fractionation of the hydrocarbon phase formed in the phase separation zone. It is preferred that the solvent stream is a relatively pure benzene stream. In many instances, the ethylbenzene which is dehydrogenated in the styrene process is produced in an alkylation unit located in the same complex. The integration of these two processes is described in detail in U.S. Pat. No. 3,525,776. In just about all of these alkylation units, a drag stream comprising benzene and non-aromatics is removed to prevent the buildup of the non-aromatics in the unit. This drag stream can be used advantageously as the solvent stream prior to being discharged from the process. It should first be treated as necessary for the removal of any water-soluble inorganic materials which would have an adverse effect if introduced into boiler tubes. In a boron trifluoride promoted benzene alkylation process, these materials are boron oxide hydrates which are typically removed by passing the drag stream through a bed of alumina.

The effluent of an ethylbenzene dehydrogenation process is typically separated in a fractionation zone such as described in U.S. Pat. No. 3,525,776. The hydrocarbonaceous phase removed from the phase separation or settling zone is passed into a first column referred to as a benzene-toluene column. This column is operated at a subatmospheric pressure to allow its operation at lower temperatures and hence reduce the rate of styrene polymerization. Various inhibitors such as elemental sulfur or 2,4-dinitrophenol are added for this same purpose. Sulfur is also introduced into the column by returning high molecular weight material separated from the bottoms stream of a styrene purification column. A more detailed description is contained in U.S. Pat. Nos. 3,476,656; 3,408,263; and 3,398,063.

There is effected within the benzene-toluene column a separation of benzene and toluene from the effluent to produce an overhead stream which is substantially free of styrene and ethylbenzene. This stream contains preferably at least 95 mole percent benzene and toluene, and may be used as the solvent stream. It may also be further fractionated to produce a substantially pure benzene stream which can then be used as the solvent stream. The bottoms stream of the benzene-toluene column is passed into a second fractionation column from which ethylbenzene is removed as an overhead product and recycled. The bottoms stream of this column is purified to obtain the styrene. The hydrocarbon stream removed from the phase separation zone may also be fractionated in a different sequence. For instance, the bottoms stream removed from the first column may be a high purity styrene stream and the ethylbenzene may be taken overhead. Syyrene may also be separated from the hydrocarbon stream by the use of liquid extraction as described in U.S. Pat. Nos. 3,424,807; 3,427,362 and 3,437,704.

The present invention may be applied to any process for the dehydrogenation of alkylaromatic hydrocarbons wherein the dehydrogenation zone effluent is condensed to form a liquid water phase and a portion of this water is to be recycled for the production of steam. The specific mode of operation of the reaction zone or the composition of the catalytic material is not determinative of the usefulness of the invention. The examples and description herein which refer specifically to the dehydrogenation of ethylbenzene are therefore not intended to so limit the invention as this process may be applied to the dehydrogenation of other alkylaromatic hydrocarbons such as diethylbenzene, ethyltoluene, propylbenzene and isopropylbenzene and also to alkylaromatic hydrocarbons having other ring structures, including naphthalenes and anthracene compounds.

The reaction zone preferably comprises two or three beds of dehydrogenation catalyst with means for the intermediate addition and admixture of steam. Suitable systems are presented in U.S. Pat. Nos. 3,498,755; 3,515,763; and 3,751,232. The catalyst beds may be contained in separate reaction vessels and may have either a cylindrical or an annular shape. Different catalysts may be used in different beds as described in U.S. Pat. No. 3,223,743. Such catalysts generally consist of one or more metallic components selected from Groups VI and VIII of the periodic table. These metallic components are typically carried on a refractory inorganic oxide material such as alumina, silica, boria or mixtures thereof. One typical catalyst comprises 85% by weight ferric oxide, 2% chromia, 12% potassium hydroxide and 1% sodium hydroxide. A second typical catalyst comprises 90% by weight iron oxide, 4% chromia and 6% potassium carbonate. Methods for preparing suitable catalysts are well known in the art. This is demonstrated by the teachings of U.S. Pat. No. 3,387,053, which describes the manufacture of a catalytic composite of at least 35 wt.% iron oxide as an active catalytic agent, from about 1 to 8 wt.% zinc or copper oxide, about 0.5 to 50 wt.% of an alkali promoter, and from about 1 to 5 wt.% chromic oxide as a stabilizer and a binding agent. Catalysts preferably employed are available commercially and are commonly referred to as "Shell 105" or "Shell 205".

Dehydrogenation conditions in general include a temperature of about 1000° F to about 1800° F and preferably about 1050° F to about 1250° F. The temperature required for any specific unit will depend on the activity of the catalyst employed. The pressure maintained within the dehydrogenation zone is generally quite low and may range from about 0 to 100 psig, with a preferred pressure range being from about 2.0 to 10 psig. The feed stream is charged to the dehydrogenation zone at a liquid hourly space velocity, based on liquid hydrocarbon charge at 60° F, of about 0.1 hr.$^{-1}$ to about 1.0 hr.$^{-1}$, and preferably from 0.2 to 0.7 hr.$^{-1}$.

As previously mentioned, the alkylaromatic to be dehydrogenated is admixed with superheated steam to counteract the temperature lowering effect of the endothermic dehydrogenation reaction. Preferably, the steam is admixed with the feed stream and also added at intermediate points within the reaction zone. As an alternative to using steam, some processes utilize indirect heat exchange of the reactants or heating elements within the catalyst bed. The steam and alkylaromatic hydrocarbon can be separately heated and then mixed prior to contacting the reactants with the catalyst, or the steam and alkylaromatic can be first commingled and then heated. When ethylbenzene is being dehydrogenated, the space velocity, the rate of steam admixture and the inlet temperature are preferably adjusted to result in the effluent of each catalyst bed having a temperature of about 1100° F. Preferably, steam is admixed with the feed stream to the dehydrogenation zone at a rate of about 0.65 to about 1.0 pound of steam per pound of ethylbenzene. A second portion is added to the effluent of the first catalyst bed at a rate of about 1.0 to about 1.2 pounds of steam per pound of effluent, and a third portion is added to the effluent of the second bed at a rate of about 0.8 to about 1.3 pounds per pound of effluent. These rates are adjusted such that the total effluent stream from the dehydrogenation zone will contain from about 3 to about 6 pounds of steam per pound of styrene.

The effluent stream removed from the dehydrogenation zone is often first heat exchanged for the dual purposes of lowering its temperature to prevent polymerization of the styrene and for the recovery of heat. The effluent stream may be heat exchanged against a make-up stream of steam, a reactant stream of this or another process or used as a heat source for fractionation. Commercially, the effluent stream is often passed through several heat exchangers for the heating of different streams. The reaction zone effluent may also be passed through a quench zone to rapidly cool it and lessen polymerization. The quench zone may be located after a heat exchange means as shown in U.S. Pat. Nos. 3,515,765 and 3,515,766, or the effluent stream may pass directly from the reactor into the quench zone as shown in U.S. Pat. No. 3,515,764. The cooling media fed to the quench zone is preferably liquid water removed from the phase separation zone. This water is not treated in the liquid-liquid extraction zone. Admixture with the extract stream also preferably lowers the temperature of the effluent stream. The temperature of the effluent stream is finally lowered sufficiently to cause the condensation of essentially all of the hydrocarbons having 6 or more carbon atoms. Preferably, the effluent stream of the reaction zone is cooled to a temperature at which a liquid phase is formed which contains at least 50 percent of the product material and 90 percent of the water in the effluent stream. When large amounts of heat are recovered from the effluent stream, a trim cooler is sufficient to cool the effluent stream to the desired temperature of about 100° to 150° F. The temperature used will be the maximum temperature consistent with the condensation of the water at the low pressure at this point.

The effluent stream is then passed into a phase separation zone wherein the effluent divides into a hydrocarbonaceous liquid phase, an aqueous liquid phase and a gaseous phase. There will be some water dissolved in the hydrocarbonaceous phase, which comprises ethylbenzene, styrene, benzene and toluene. There will also be some hydrocarbons dissolved in the aqueous liquid phase. The composition of the gaseous phase will vary with the temperature imposed, but will comprise hydrogen, methane, ethane, ethylene, carbon monoxide, carbon dioxide and other light gases which are formed in the process. The gaseous phase will separate from the liquid phase rather easily and is vented off. The gaseous phase is often treated to recover heavier hydrocarbons, especially benzene prior to being removed as the off-gas stream. A suitable treating method is to compress this stream to about 50 psig and then to cool it to about 100° F. The liquid material in the effluent is passed through a quiescent portion of the phase separation zone and the two resulting liquid phases are separated by decantation. The design and operation of phase separation zones is well understood by those skilled in the art. For instance, U.S. Pat. No. 3,702,346 teaches the beneficial higher selectivity derived in a similar process by maintaining the product settler at a subatmospheric pressure, preferably in the range of from about 200 mm. Hg to about 600 mm. Hg absolute.

In accordance with the above description, the preferred embodiment of the invention may be characterized as a process for the catalytic dehydrogenation of alkylaromatic hydrocarbons which comprises in cooperative combination the steps of admixing a feed stream comprising an alkylaromatic hydrocarbon with steam and contacting the resulting admixture with a dehydrogenation catalyst within a reaction zone maintained at dehydrogenation conditions and effecting the formation of an effluent stream comprising an alkenylaromatic hydrocarbon and steam, cooling the effluent stream and effecting at least a partial condensation of the effluent stream, further cooling the effluent stream by admixing the effluent with a liquid hydrocarbon stream comprising benzene, the alkenylaromatic hydrocarbon and dissolved water, passing the effluent stream into a phase separation zone and effecting the formation of a hydrocarbonaceous liquid phase and an aqueous liquid phase comprising the alkenylaromatic hydrocarbon, passing a water stream comprising at least a portion of the aqueous liquid phase into a liquid-liquid extraction zone and contacting the water stream with a solvent stream to effect a transfer of substantially all of the alkenylaromatic hydrocarbon contained in the water stream into the solvent stream and the formation of an extract stream comprising benzene, the alkenylaromatic hydrocarbon and dissolved water, and admixing at least a portion of the extract stream with the effluent stream as the liquid hydrocarbon stream.

I claim as my invention:

1. A process for the dehydrogenation of ethylbenzene which comprises in cooperative combination the steps of:
   a. admixing a feed stream comprising ethylbenzene with steam and contacting the resulting mixture with a heterogeneous fixed bed dehydrogenation catalyst within a reaction zone maintained at dehydrogenation conditions and effecting the formation of an effluent stream comprisng styrene, ethylbenzene and steam;
   b. cooling the effluent stream and effecting partial condensation of said stream;
   c. effecting a further cooling of said effluent stream by admixture of said effluent stream with a liquid hydrocarbon stream comprising benzene, styrene and dissolved water;
   d. passing said admixed effluent stream into a phase separation zone and effecting the formation of a hydrocarbonaceous phase comprising styrene, benzene, toluene and ethylbenzene and an aqueous phase comprising styrene;
   e. passing at least a portion of said aqueous phase into a liquid-liquid extraction zone and contacting said aqueous phase with a solvent stream comprising benzene to effect a transfer of substantially all the styrene contained in the aqueous phase into said solvent stream to form an extract stream comprising benzene, styrene and dissolved water;
   f. fractionating at least a portion of said extract stream comprising benzene, styrene and dissolved water to produce said solvent stream comprising benzene; and,
   g. admixing at least a portion of said extract stream as the liquid hydrocarbon stream of step (c) with said effluent stream.

2. The process of claim 1 further characterized in that a raffinate water stream is removed from the liquid-liquid extraction zone and passed into a steam generation zone.

3. A process for the dehydrogenation of ethylbenzene which comprises in cooperative combination the steps of:
   a. admixing a feed stream comprising ethylbenzene with steam and contacting the resulting admixture with a fixed bed dehydrogenation catalyst within a reaction zone maintained at dehydrogenation conditions and effecting formation of an effluent stream comprising styrene and steam;
   b. cooling the effluent stream and effecting at least a partial condensation of said effluent stream;
   c. passing the effluent stream into a phase separation zone and effecting the formation of a hydrocarbonaceous liquid phase and an aqueous liquid phase comprising styrene, benzene and dissolved water;
   d. passing at least a portion of said aqueous liquid phase into a liquid-liquid extraction zone and contacting said aqueous liquid phase with a solvent stream comprising benzene to effect transfer of substantially all of the styrene contained in said liquid aqueous phase into said solvent stream to form an extract stream comprising benzene, styrene and dissolved water wherein at least a portion of said extract stream comprising benzene, styrene and dissolved water is fractionated to produce said solvent stream; and,
   e. passing at least a portion of said extract stream into said phase separation zone of step (c).

* * * * *